United States Patent [19]

Sabbah et al.

[11] Patent Number: 5,419,332
[45] Date of Patent: May 30, 1995

[54] MAPPING OF FLOW PARAMETERS

[76] Inventors: Benjamin Sabbah; Avraham Bruck; Zvi Friedman, all of c/o Elscint Ltd. P.O.B. 550, Haifa 31004, Israel

[21] Appl. No.: 183,869

[22] Filed: Jan. 21, 1994

Related U.S. Application Data

[63] Continuation-in-part of Ser. No. 100,163, Aug. 2, 1993, Pat. No. 5,383,463.

[51] Int. Cl.⁶ .............................................. A61B 8/00
[52] U.S. Cl. .............................................. 128/661.09
[58] Field of Search .................. 128/661.07, 661.08, 128/661.09, 661.10, 660.05

[56] References Cited

U.S. PATENT DOCUMENTS

| | | | |
|---|---|---|---|
| 3,940,731 | 2/1976 | Cooper et al. | 128/661.09 |
| 4,583,409 | 4/1986 | Lannuzel et al. | 128/661.09 |
| 5,050,611 | 9/1991 | Takamizawa et al. | |
| 5,090,413 | 2/1992 | Yoshioka. | |
| 5,107,841 | 4/1992 | Sturgill | 128/661.09 |

*Primary Examiner*—George Manuel
*Attorney, Agent, or Firm*—Sandler, Greenblum & Bernstein

[57] ABSTRACT

Automatic mapping of flow parameters in a ultrasound diagnostic imaging system including the steps of: selecting a region of interest (ROI), transmitting ultrasound signals along at least one line traversing blood vessels in the ROI, applying a train of pulses along each of said at least one line during a heart cycle, generating a spectral density function as a function time, displaying selected blood flow characteristics determined from said spectral density function.

21 Claims, 2 Drawing Sheets

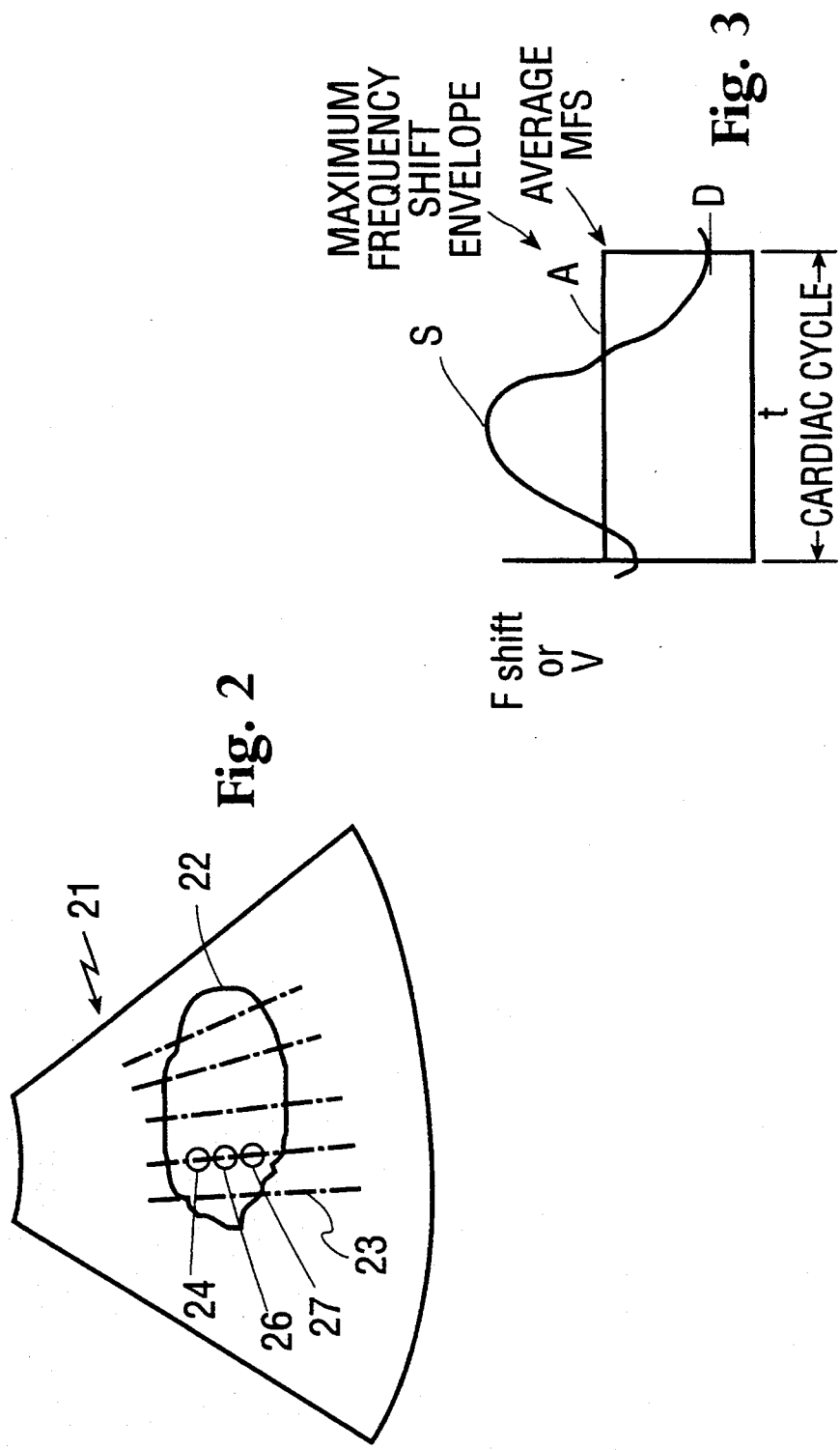

MAPPING OF FLOW PARAMETERS

The present invention is a continuation in part application of the application bearing Ser. No. 08/100,163 filed on Aug. 2, 1993 now U.S. Pat. No. 5,383,463.

FIELD OF THE INVENTION

The present invention relates to ultrasonic diagnostic imaging systems and more particularly, to such systems which are capable of displaying a plurality of flow parameters alone or superimposed on an anatomical image.

BACKGROUND OF THE INVENTION

Diagnostic ultrasound imaging systems provide a comprehensive evaluation of a subject's health condition, The efficacy of ultrasound techniques have resulted in the widespread acceptance of ultrasound imaging by both patients and physicians. In general, diagnostic ultrasound imaging systems generate images of anatomical structures within the patient by transmitting ultrahigh frequency soundwaves (typically in the order of 3.0–10.0 MHz) and then analyzing the waves reflected from the body structure. The most widely used ultrasonic diagnostic systems display structural information of organs in the form of two-dimensional images of selected cross sections of the organ. Typically, the ultrasound is swept across the organ in the form of a "cross sectional scan". The scan is ordinarily performed in real time so that the dynamics of anatomical structures can be visualized.

In presently available ultrasound systems, in addition to anatomical information, blood flow information is often provided by utilizing the Doppler principle, or other known techniques. A beam, comprising pulses of ultrasonic energy is directed toward a blood vessel in which blood flow information is desired. For example, a scan is conducted on the placenta wherein the blood vessels between the mother and the embryo are interfaced, but not joined. To use the Doppler principle, the beam of ultrasonic energy is directed toward a blood vessel. Moving blood cells reflect the ultrasound energy and either increase or decrease the frequency of the reflected energy depending on the direction of the blood flow in accordance with the well known Doppler principle.

The magnitude of the frequency shift and the direction of the shift are detected so that the velocity and the direction of the blood flow may be ascertained. Such Doppler ultrasound apparatus also typically provides the usual anatomical information using conventional diagnostic ultrasound techniques.

One form of examination is to thoroughly interrogate blood flow at a certain point, typically 1–2 mm in size as a function of time for periods of time that typically are several heart cycles in length. The certain points interrogated are often referred to as "gates" or "sample volumes". The information obtained this way is mainly the flow velocity, volume flow and velocimetry indices: such as PI (Pulsitility Index), RI (Resistance Index), etc. Another form of examination is to interrogate a multiplicity of gates during the same time period. Thus, either one gate is given an extensive interrogation or a plurality of gates are cursorily interrogated during the interrogation period.

The ultrasound equipment now in use, however, fails to provide for mapping of flow indicies which describe the nature of the flow other than average or maximum velocity of the flow. Thus, while the analysis of blood flow using ultrasound has found a variety of applications in recent years, it has not been used to perform effective mapping of flow parameters other than average or maximum velocity.

One example of the application of flow indicies, is to study blood perfusion in the placenta. The studies of this type are used to monitor fetal growth based on the fact that normal fetal growth depends on an adequate supply of oxygen and nutrients which are generally carried to the fetus by the fetal blood through the umbilical placental circulation throughout pregnancy. The studies of the umbilical placental circulation of the human fetus have been greatly facilitated by the use of the aforementioned ultrasound analysis of the flow. Recently, there have been some studies wherein the waveforms of the flow velocity have been studied. However, most of these studies have focused on the umbilical artery. The characteristics of the fetal circulation further downstream to the umbilical artery have seldom been studied due to practical reasons and no effective method of using clinical ultrasound has been developed until now to augment such studies.

Another example where studies of flow parameter characteristics would be beneficial is the examination of whether or not a suspicious mass might be a malignant tumor. It is known that malignant tumorous masses are generally accompanied by anglogenesis which results in increased diastolic blood flow. This blood flow can be measured and characterized with spectral flow analysis. For example, in the past, procedures using spectral Doppler for characterizing tumors have not proven fully successful because the required thorough investigation of the tumor area was not practical with present state of the art. Presently the blood vessels are detected using color flow imaging. Each point is then analyzed separately using spectral analysis. This is a very tedious and time consuming procedure, and is therefore limited to a relatively small number of points, which may sometimes be insufficient for a reliable diagnosis.

BRIEF DESCRIPTION OF THE INVENTION

In accordance with a preferred aspect of the present invention, a spectral flow analysis ultrasound system that maps blood flow indicies for diagnosing blood perfusion in anatomical organs such as blood flow characteristics in the kidney, placenta, peripheral vessels is provided, said system comprising the steps of:
  scanning a patient to acquire a two dimensional image to select an area under study.
  analyzing blood flow characteristics in the selected area, by:
    transmitting a plurality of ultrasound pulses along at least one ultrasound beam and analyzing a plurality of gates for blood flow during at least one heart cycle,
    sampling each beam several times at given intervals to obtain echo spectral data,
    selecting the data which corresponds to flow,
    eliminating data from stationary reflectors,
    performing a spectral analysis on the data to obtain spectral data.
    storing the spectral data for further processing,
    converting said stored spectral data to blood flow indicies, and
    displaying a distribution of the resulting blood flow indicies on the two dimensional image.

The prior art did provide some studies of flow indicies. However, this was accomplished manually using colored flow mapping methods mainly as a guide to detect flow. Each point at which flow was detected was then individually investigated by a more detailed interrogation at that point obtaining spectral waveforms and subsequently analyzing them. A major deficiency with the prior art systems is that in the past it has been too time consuming to be practical; because, obtaining the blood flow indicies throughout the organ is a slow and meticulous process since each point must be sequentially interrogated and analyzed.

It is a feature of the present invention to provide mapping of flow indicies by determining the flow through a plurality of gates traversed by a single beam or traversed by a plurality of beams for determining the flow indicies at each of the gates, practically simultaneously whereby the time efficiency of the system makes it clinically effective.

BRIEF DESCRIPTION OF THE DRAWINGS

The above mentioned and other objects and features of the present invention will be best understood when considered in the light of the following description of a preferred embodiment of the present invention wherein:

FIG. 2 is a showing of a sector scan with a multiplicity of gates, and

FIG. 3 is a typical spectral density function of a variable that is proportional to velocity as a function of time shown as a maximum frequency or velocity shift envelope.

In FIG. 1, a Doppler system is shown by way of example. It must be understood that other velocity determining systems can be used within the scope of the invention. In the exemplary Doppler system an ultrasound Doppler channel 11 is shown in block diagram form. Channel 11 is shown as comprising a transmitting—receiving unit 12 operated in conjunction with oscillator 13. The transmitting portion of the unit 12 transmits pulses of ultrasound waves, typically in the order of 3-10 MHz; through the transducer 14. The transducer 14 also acts to receive the echoes obtained from the soundwaves when they are reflected by organs in patient or subject 15 in the path of the transmitted soundwaves. The receiving portion of unit 12 receives these echoes and transmits them to a demodulator 16 and to a 2D imaging channel 17. The demodulator 16 provides in phase (I) signals and quadrature (Q) signals. The signals from the demodulator 16 and the 2D imaging channel are sent to a processor 18 for image processing. The processed signals are sent to display unit 19 which displays images 21.

Figure 1:
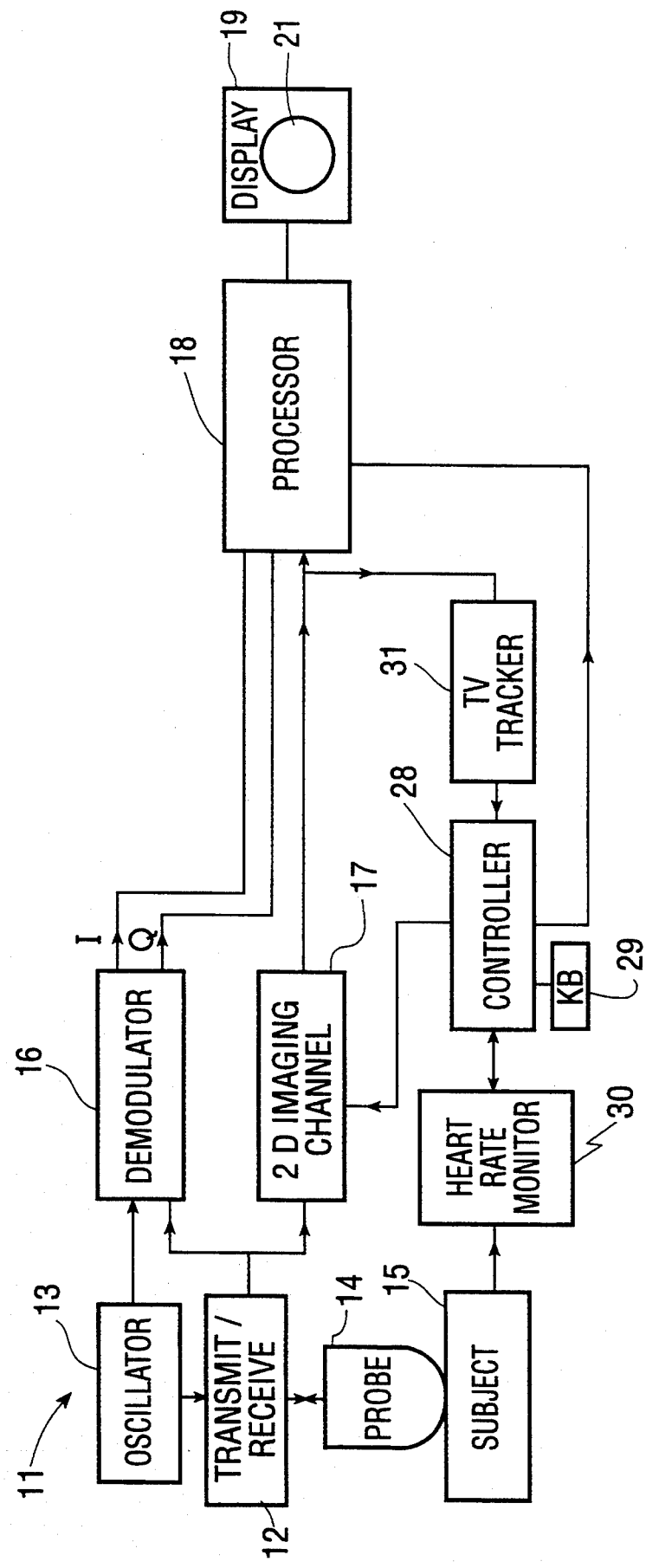
FIG. 1 is a block diagram showing of an ultrasound Doppler system including the invention.

The displayed image 21, as shown in FIG. 2, generally includes an anatomical image of a sector scan that encompasses a region of interest (ROI) 22. The ROI 22 is traversed by a plurality of beams such as beam 23. Along each of the beams, gates such as gates 24, 26 and 27 are located where the Doppler indicates blood flow: i.e., blood vessels carrying blood. The received Doppler information at each of the sampled points is spectrally processed in processor 18 and the various velocimetry indices (or other indices; e.g., spectral broadening) computed. Results can then be displayed as a color map overlay on the two dimensional grayscale image. Also, the spectrum can be displayed at each gate for validation.

The processing of the flow information is performed within tile processor 18 under the control of controller 28 after the user determines and inputs tile blood flow parameter desired using for example keyboard (KB) 29. The processor 18 among other things determines the maximum frequency shift curve or envelope for a cardiac cycle as shown in FIG. 3. It may be advantageous, though not required for the cardiac cycle of the patient 15 to be monitored, determined or, where applicable gated, by the heart rate monitor 30. The cardiac cycle extends from the minimum velocity of a diastolic period D (or ending diastolic period) and includes a maximum velocity S that occurs during the intervening systolic period. The average of the maximum frequency shift is shown as A.

If the user inputs the pulsitility index, $[PI=(S-D)/A]$ for example, then the following procedure is used:
1) At each gate the maximum frequency shift envelope is generated from the measurements of frequency shift versus time during a heart cycle at each gate.
2) The maximum velocity values of the envelope is noted.
3) The end systolic value D of the envelope is noted,
4) The average value A of the maximum frequency shift envelope is noted.
5) The end systolic value D is subtracted from the peak systolic value S;
6) The difference is divided by the average value A of the maximum frequency shift envelope; the quotient is the pulsitility index, PI.

Another parameter that may be of interest is the resistance index RI, where $RI=(S-D)/S$. There, the same two parameters (S,D) are subtracted one from the other, but the divisor is the peak systolic values.

The systolic-to-diastolic ratio may be determined which comprises dividing the peak systolic value S by the end diastolic value D. Another characteristic of interest is the diastolic average ratio which may be determined by dividing the end diastolic value D by the average value A of the maximum frequency shift over the cardiac cycle.

Whereas, in the past were the mean flow velocities were displayed in quasi-real time at the rate of four to twenty frames/sec, it is now proposed to spend the complete heart cycle on each group of selected lines to assure acquiring all data required for mapping the flow parameters. Each of the gates may be interrogated to provide the flow parameter information in parallel.

A typical mode of operation will be that the user preselects a region of interest which the system will then investigate at all points. Since the time required for a full spectrum is in the order of 1-3 sec.; i.e., one to three cardiac cycles, a multigate system which investigates all the points along the scan lines or beams during the same heart cycles is used.

Conventional color flow imaging systems are multigate systems. In the conventional application of color flow imaging where mean flow velocities are displayed in quasi-real time at a rate of 4-10 train of pulses per second, the number of echoes transmitted along one scan line is limited to 4-16 scan lines. The time for a scan line is 1-4 msecs. This time is too short for the calculation of flow parameters. In order to produce the maximum frequency shift envelope, the scanning procedure is changed. The scanning is performed on a group of lines for 1-3 secs. This time is sufficient to acquire all the data needed for a full spectral analysis, for all the points in the image area covered by these lines.

The processor 18 preferably also prevents misalignment between the sector scan (2 D gray scale) image and the flow parameters showing on the sector scan image. This involves the simultaneous generation of both the sector scan image and the Doppler image.

Another misalignment prevention procedure includes the step of projecting and locking cross hairs onto the region of interest in the scan sector image. The process of locking each of the sample volumes (gates) to the specific location within the organ is accomplished using a special image board, known to those skilled in the art of image processing as an image TV tracker, shown at 31 in FIG. 1. Such a board automatically identifies outstanding details in the gray scale 2D image in each of the different scans, and moves the Doppler gates such that their relative positions remain fixed. This also compensates for effects that may be caused by the relative motion between the tissue and the transducer.

Thus, a novel ultrasound diagnostic imaging system has been disclosed. Although preferred embodiments of the apparatus have been described in some detail, it is to be understood that various changes could be made by persons skilled in the art without departing from the spirit and scope of the invention as defined by the attached Claims.

What is claimed is:

1. An ultrasound diagnostic imaging method that provides blood flow parameters for analyzing blood flow, said method comprising the steps of:
   selecting a region of interest in a sector scan image;
   transmitting ultrasound signals along at least one line traversing said selected region of interest;
   locating a plurality of gates to define gated sections along each of said at lest one line where blood vessels are traversed;
   said transmitted ultrasound signals comprising a train of pulses transmitted along each of said at least one line for transmission through said gates;
   receiving reflected spectral signals back from said gates,
   converting said reflected spectral signals to a spectral density function of a variable that is proportional to velocity as a function of the time that extends over at least one heart cycle for each of said gates;
   selecting at least one blood flow indice other than velocity to be determined; and
   determining the flow indices from said spectral density function.

2. The ultrasound dianostic imaging method of claim 1 wherein said spectral density function is a maximum velocity shift envelope.

3. The ultrasound imaging method of claim 1 wherein said spectral density function is a maximum frequency shift envelope.

4. The ultrasound diagnostic imaging method of claim 1 wherein the step of transmitting the train of pulses along each of said lines comprises transmitting said train of pulses along of each of said lines individually for transmission through said gates during said at least one heart cycle.

5. The ultrasound diagnostic imaging method of claim 1 wherein the application of the train Doppler pulses along each of said lines individually are transmitted through all of said gates in each of said lines during said at least one heart cycle.

6. The ultrasound diagnostic imaging method of claim 1 wherein the step of applying a train of pulses along each of said lines comprises gating the train of pulses responsive to said at least one heart cycle.

7. The ultrasound diagnostic imaging method of claim 1 including the step of displaying the selected blood flow parameter values in a plurality of colors wherein a first color is used below a certain value of the at least one selected blood flow parameter and a second color is used above that certain value.

8. The ultrasound diagnostic imaging method of claim 1 including the step of displaying the selected blood flow parameter values in a plurality of colors wherein there is a one-to-one correspondence between said values and said colors.

9. The ultrasound diagnostic imaging method of claim 1 including the step of displaying the selected blood flow parameter values in a plurality of shades wherein a first shade is used below a certain value of the selected blood flow parameter and a second shade is used above said certain value of the selected blood flow parameter.

10. The ultrasound diagnostic imaging method of claim 1 including the step of displaying the selected blood flow parameter values in a plurality of shades wherein there is a one-to-one correspondence between said values and said shades.

11. The ultrasound diagnostic imaging method of claim 1 wherein scanning of the region of interest is performed over a plurality of lines on a sequential line after line basis.

12. The ultrasound diagnostic imaging method of claim 11 including the step of transmitting at least one ultrasound pulse out of the complete number of pulses to be transmitted over each line prior to transmitting over a next line in the sequential line after line basis.

13. The ultrasound diagnostic imaging method of claim 11 including the step of transmitting the complete number of pulses to be transmitted over each line prior to transmitting over the next line.

14. The ultrasound diagnostic imaging method of claim 1 including a step of preventing misalignment between the sector scan image and the flow parameter image.

15. The ultrasound diagnostic imaging method of claim 14 wherein the step of preventing misalignment between the sector scan image and the flow parameter image comprises simultaneously generating both the sector scan image and the flow parameter image throughout the region of interest to provide a flow parameter image superimposed on the two-dimensional sector scan image.

16. An ultrasound diagnostic imaging method that prevents misalignment between a sector scan image in the flow parameter image, such system comprising the steps of:
   selecting a region of interest in an original sector scan image;
   transmitting ultrasound signals along at least one line traversing said selected region of interest;
   locating a plurality of gates to define gated sections along each of said at least one line where blood vessels are traversed;
   said ultrasound signals comprising a train of pulses along each of said at least one line to be transmitted through said gates;
   receiving spectral signals back through said gate;

converting said spectral signals to a spectral density function of a variable that is proportional to the velocity as a function of time for each of said gates;

selecting at least one blood flow parameter to be determined;

determining the selected blood flow parameter form said spectral density function; and locking cross-hairs on to the region of interest of the original sector scan image to correlate the original sector scan image through a series of sector scan images that is taken during the pulse scanning and reduce artifacts caused by relative motion between tissues in the sector scan image and the transducer used for transmitting the ultrasound signals along said at least one line.

17. The ultrasound diagnostic imaging system of claim 16 wherein said spectral density function is a maximum velocity shift envelope.

18. The ultrasound diagnostic imaging system of claim 16 wherein said spectral density function is a maximum frequency shift envelope.

19. An ultrasound diagnostic imaging method that provides blood flow parameters for analyzing blood flow, said method comprising the steps of:

selecting a region of interest in a sector scan image;

transmitting ultrasound signals along at least one line traversing said selected region of interest;

locating a plurality of gates to define gated sections along each of said at least one line where blood vessels are traversed;

said transmitted ultrasound signals comprising a train of pulses transmitted along each of said at least one line for transmission through said gates;

receiving reflected spectral signals through said gates;

converting said reflected spectral signals to a spectral density function of a variable that is proportional to the velocity as a function of time that extends over at least one half cycle for each of said gates;

selecting at least one blood vessel indice to be determined;

determining the selected blood flow indices from said spectral density function, and scanning the region of interest on an interlaced line basis.

20. An ultrasound diagnostic imaging method of claim 19 including the step of transmitting at least one ultrasound pulse of the complete number of pulses to be transmitted over each line prior to transmitting over a next line in the interlaced line after line basis.

21. An ultrasound diagnostic imaging method that provides blood flow parameters for analyzing blood flow, said method comprising steps of:

selecting a region of interest in a sector scan image;

transmitting ultrasound signals along at least one line traversing said selected region of interest;

locating a plurality of gates to define gated sections along each of said at least one line where blood vessels are traversed;

said transmitted ultrasound signals comprising a train of pulses transmitted along each of said ate least one line for transmission through said gates;

receiving reflected spectral signals back through said gates;

converting said reflected spectral signals to a spectral density function of a variable that is proportional to velocity as a function of time that extends over at least one heart cycle for each of said gates;

selecting at least one flow parameter to be determined;

determining the selected flow parameter from said spectral density function; and locking a TV tracker onto the image to correlate the original image through a series of two-dimensional images taken during the scanning, to reduce artifacts caused by the relative motion of the tissue and the transducer.

* * * * *

UNITED STATES PATENT AND TRADEMARK OFFICE
CERTIFICATE OF CORRECTION

PATENT NO. : 5,419,332
DATED : May 30, 1995
INVENTOR(S) : Sabbah et al

It is certified that error appears in the above-indentified patent and that said Letters Patent is hereby corrected as shown below:

On the title page, add [73] Assignee: Elscint Ltd. Haifa, Israel

Signed and Sealed this

Twenty-eighth Day of November 1995

Attest:

BRUCE LEHMAN

*Attesting Officer*    *Commissioner of Patents and Trademarks*